(12) United States Patent
Weber et al.

(10) Patent No.: US 11,246,967 B2
(45) Date of Patent: Feb. 15, 2022

(54) BREASTSHIELD UNIT

(71) Applicant: MEDELA HOLDING AG, Baar (CH)

(72) Inventors: Beda Weber, Sins (CH); Martin Thüring, Sins (CH); Mario Rigert, Buchrain (CH); Armin Felber, Lucerne (CH)

(73) Assignee: MEDELA HOLDING AG, Baar (CH)

(*) Notice: Subject to any disclaimer, the term of this patent is extended or adjusted under 35 U.S.C. 154(b) by 329 days.

(21) Appl. No.: 16/335,540

(22) PCT Filed: Sep. 14, 2017

(86) PCT No.: PCT/EP2017/073155
§ 371 (c)(1),
(2) Date: Mar. 21, 2019

(87) PCT Pub. No.: WO2018/054758
PCT Pub. Date: Mar. 29, 2018

(65) Prior Publication Data
US 2020/0016306 A1    Jan. 16, 2020

(30) Foreign Application Priority Data
Sep. 22, 2016 (EP) .................................. 16190122

(51) Int. Cl.
*A61M 1/06* (2006.01)
*A61M 39/24* (2006.01)

(52) U.S. Cl.
CPC ............ *A61M 1/064* (2014.02); *A61M 39/24* (2013.01); *A61J 2200/76* (2013.01);
(Continued)

(58) Field of Classification Search
CPC ........ A61M 1/064; A61M 1/06; A61M 1/062; A61M 2205/3306; A61M 2205/3334;
(Continued)

(56) References Cited

U.S. PATENT DOCUMENTS 4,832,689 A * 5/1989 Mauerer ........... A61M 5/16809
604/67
8,606,596 B1 * 12/2013 Bochenko .............. G16H 20/10
705/2
(Continued)

FOREIGN PATENT DOCUMENTS

CN 201745123 U 2/2011
CN 204890738 U 12/2015
(Continued)

OTHER PUBLICATIONS

International Search Report for Application No. PCT/EP2017/073155, dated Nov. 28, 2017.

*Primary Examiner* — Jenna Zhang
(74) *Attorney, Agent, or Firm* — Marshall, Gerstein & Borun LLP

(57) ABSTRACT

A breast shield unit of a breast pump for expressing human breastmilk comprises a breast shield to be placed onto a mother's breast, a breastmilk collection container for receiving expressed breastmilk, an adapter for connecting the breast shield to the breastmilk collection container and a valve head. A breastmilk channel extends from the breast shield into the breastmilk collection container through the adapter and the valve head. The valve head includes a valve which closes and opens the breastmilk channel during the pumping action, wherein a fill level sensor for measuring a fill level of the breastmilk collection container is arranged in the valve head. The breast shield unit according to the invention facilitates a fill level measurement without a structural change of the breast shield and breastmilk collection container. Moreover, it facilitates data interchange with external information storage and/or information processing units.

19 Claims, 2 Drawing Sheets

(52) U.S. Cl.
CPC ............... *A61M 2039/244* (2013.01); *A61M 2205/3306* (2013.01); *A61M 2205/3334* (2013.01); *A61M 2205/3382* (2013.01); *A61M 2205/3389* (2013.01); *A61M 2205/3553* (2013.01); *A61M 2205/3569* (2013.01); *A61M 2205/3584* (2013.01); *A61M 2205/50* (2013.01)

(58) Field of Classification Search
CPC .. A61M 2205/3382; A61M 2205/3389; A61M 2205/3379
See application file for complete search history.

(56) References Cited

U.S. PATENT DOCUMENTS

| | | | |
|---|---|---|---|
| 2011/0257579 A1* | 10/2011 | Rossi | A61M 1/36 604/6.15 |
| 2015/0038945 A1 | 2/2015 | McCabe | |
| 2016/0082165 A1* | 3/2016 | Alvarez | A61M 1/062 604/74 |
| 2016/0082166 A1 | 3/2016 | Guthrie et al. | |
| 2016/0220743 A1 | 8/2016 | Guthrie et al. | |
| 2016/0296681 A1* | 10/2016 | Gaskin | A61M 1/06 |
| 2017/0182231 A1 | 6/2017 | Aalders et al. | |

FOREIGN PATENT DOCUMENTS

| | | |
|---|---|---|
| EP | 0 266 590 A2 | 5/1988 |
| WO | WO-2006/003655 A1 | 1/2006 |
| WO | WO-2009/081313 A1 | 7/2009 |
| WO | WO-2014/161099 A1 | 10/2014 |
| WO | WO-2015/120321 A1 | 8/2015 |

* cited by examiner

BREASTSHIELD UNIT

CROSS-REFERENCE TO RELATED APPLICATION

The present application is the US national phase of International Application No. PCT/EP2017/073155, filed Sep. 14, 2017, which claims priority to European Application No. 16190122.8, filed Sep. 22, 2016. The priority application, EP 16190122.8, is hereby incorporated by reference in its entirety.

TECHNICAL FIELD

The present invention relates to a breast shield unit of a breast pump for expressing human breastmilk and to a valve head of such a breast shield unit.

PRIOR ART

A breast shield is placed onto the mother's breast for expressing human breastmilk, said breast shield being connected to a vacuum pump in order to apply a cyclically varying negative pressure to the breast. From the breast shield, the expressed breastmilk reaches a breastmilk collection container through a breastmilk channel. In order to keep the dead volume during expression as small as possible, a breastmilk channel from the breast shield to the breastmilk collection container is usually provided with a check valve which opens for admitting the expressed breastmilk into the breastmilk collection container. This check valve is preferably arranged at an adapter which connects the breast shield to the breastmilk collection container and also, usually, the breast shield to the vacuum pump or to a vacuum tube leading to the vacuum pump. The check valve may be arranged at a valve head which is connected in a secure or detachable manner to the adapter, the latter also being referred to as coupling part.

By way of example, such an apparatus is known from WO 2014/161099 A1. The breast shield unit described therein comprises a flow sensor which detects the change of a valve flap of the check valve such that deductions may be drawn about the flow of the breastmilk from the breast shield into the breastmilk collection container.

US 2016/0082166 A1 discloses an adapter comprising a sensor for detecting the breastmilk production, the sensor communicating with a mobile data receiver or with the breastmilk pump by way of a wireless connection.

WO 2006/003655 A1 shows a nipple cap which is placed onto the mother's breast when breastfeeding a baby. This nipple cap is provided with a sensor which measures the breastmilk volume emerging from the breast.

WO 2009/081313 A1 discloses a breast shield comprising at least one sensor for optimizing and personalizing the pumping process.

These breast shield units have a relatively complicated, and hence cost-intensive, structure. However, since the breast shields and breastmilk collection containers often may, or must, only be used once or a few times, it should be possible to manufacture these as cost-effectively as possible and/or they should be easy to clean.

SUMMARY OF THE INVENTION

It is therefore an object of the invention to develop a breast shield unit which is as cost-effective as possible but nevertheless permits capture of the expressed amount of breastmilk.

The breast shield unit, according to the invention, of a breast pump for expressing human breastmilk comprises a breast shield to be placed onto a mother's breast, a breastmilk collection container for receiving expressed breastmilk, an adapter for connecting the breast shield to the breastmilk collection container and a valve head. A breastmilk channel extends from the breast shield into the breastmilk collection container through the adapter and through the valve head. The valve head comprises a valve which closes and opens the breastmilk channel during the pumping action, wherein a fill level sensor for measuring a fill level of the breastmilk collection container is arranged in the valve head.

Since the fill level sensor is arranged in the valve head, the breast shield, the adapter and the breastmilk collection container may have cost-effective embodiments. In particular, it is possible to use standard parts. It is further advantageous that the valve head may be embodied in such a way that it may be used as an accessory in already available breast shield units. As a result, a redesign of known breast shield units becomes superfluous.

Preferably, the breastmilk collection container has a rigid or semi-rigid embodiment. It is preferably a breastmilk bottle which may be sealed in an airtight manner with a lid after removing the valve head, the adapter and the breast shield. Preferably, the same bottle may be used together with a suction unit, to be placed thereon during use, as a suction bottle for administering the breastmilk to an infant.

A precise measure of the actually available breastmilk is obtained by measuring the fill level in the breastmilk collection container. The measurement is preferably performed during the pumping action. The specification in relation to the fill level is preferably updated during the pumping action in a timely manner.

The measurement data may be forwarded to an evaluation unit and/or a controller and/or a display of the breast pump, either as raw data or as data which was already evaluated by means of an electronics unit integrated in the valve head. In a simple embodiment, the breast pump merely indicates these data. In other embodiments, the data are used in addition, or as an alternative, to the current or subsequent control of the pump, for example in order to automatically switch from a stimulation mode into an expression mode, or vice versa. In further embodiments, the data are alternatively, or additionally, used for automatically changing the pump parameters or the patterns of the vacuum curves, with this also being carried out for the current pumping action and/or for a subsequent pumping action, depending on embodiment.

The raw data and/or the evaluated data may also be transmitted to other receivers, for example to a smart device such as a smartphone or to another personal machine of the mother. This facilitates capturing the fill level amount, even if the breastmilk collection container cannot be seen by her. Moreover, the data may be directly supplied to the Internet, for example a cloud, in order also to be available to third parties.

The expressed breastmilk volume may be determined thanks to measuring the fill level amount. The breastmilk flow may also be detected by differentiating the volume signal.

Preferably, the fill level sensor is a distance sensor for measuring a distance from a surface of the expressed breastmilk situated in the breastmilk collection container, i.e. the pool of breastmilk situated in the container. The fill level can easily be measured in this way without the container itself needing to be provided with a fill level sensor and without the breastmilk needing to be contacted by mechanical means.

In particular, a time-of-flight sensor, also referred to as TOF sensor, is suitable as a fill level sensor. It was found that such TOF sensors are suitable for measuring the fill level of breastmilk even though, for example, they are unsuitable for measuring the fill level of water.

The distance sensor, in particular the TOF sensor, permits a distance measurement to be carried out from the sensor to the fill level height within the breastmilk collection container. To the extent that the geometry of the breastmilk collection container is known, preferably if the position angle of the breastmilk collection container in three-dimensional space is additionally known, this allows the fill level and hence the breastmilk volume to be calculated.

If use is made of a TOF sensor, an optical connection from the sensor to the opposite base of the breastmilk collection container is necessary. Preferably, the TOF sensor is positioned in such a way that it is situated on a longitudinal central axis of the breastmilk collection container. Preferably, this longitudinal central axis forms an axis of rotational symmetry of the breastmilk collection container.

In a simple embodiment, only the fill level sensor is arranged in the valve head, said fill level sensor measuring the fill level of the breastmilk in the container as a parameter. However, at least one additional sensor is preferably present in the valve head; preferably, two or more additional sensors are present for measuring further parameters.

By way of example, such an additional sensor is a flow sensor which measures the flow through the valve. By way of example, this flow sensor is an optical sensor which detects a deflection of a valve flap of the valve. Preferably, the sensor is a photoelectric barrier which detects the position of the valve flap. Preferably, a protruding wing is arranged on the valve flap to this end, said wing penetrating the light path of the photoelectric barrier. By way of example, such a flow sensor is disclosed in WO 2014/161099.

This additional measurement of the flow facilitates a correction of the fill level measurement by the fill level sensor, particularly if only small volumes of breastmilk are situated in the breastmilk collection container. Also, it is possible to use this flow sensor during movements of the breastmilk collection container in order to correct the measurements of the fill level sensor, which is inaccurate during this period of time, or to replace them completely. Furthermore, this flow sensor may be used as a monitoring means which determines whether the valve has even opened or how often and/or when it opens. These specifications may be used to control the fill level sensor. By way of example, a fill level measurement is superfluous when the valve has not opened and hence no new breastmilk has reached the breastmilk collection container.

Alternatively, or additionally, a position sensor is preferably present as a further sensor, said position sensor detecting the position of the breastmilk collection container in three-dimensional space and hence the tilt position thereof in three-dimensional space. In particular, an acceleration sensor is suitable as position sensor. The data from the position sensor are preferably used to compensate the signals from the fill level sensor in tilt positions of the breastmilk collection container. The position sensor is preferably additionally used to determine whether the breastmilk collection container even is in a position to ensure a meaningful fill level measurement.

The fill level sensor and at least the position sensor, preferably all other further sensors as well, are preferably arranged with a fixed position in relation to one another in the valve head.

The signals, which are also referred to as raw data, from the fill level sensor and, if present, from the at least one further sensor, are preferably directly forwarded to external units, such as e.g. to an evaluation and control unit of the breast pump or to a different external evaluation unit.

However, an electronics unit for processing the signals from the fill level sensor is preferably arranged in the valve head. Preferably, this internal electronics unit also processes the signals of the at least one further sensor, if present.

Preferably, the electronics unit is embodied to interchange data with at least one of the following units: a breast pump, a "smart device", such as a smartphone, which is updated from an information technology point of view; an external data processing unit such as a personal computer; cloud; Internet, Internet access unit.

For the simple use of the valve head, the latter preferably is embodied without wires to the outside and, in terms of electronic connectors, without a connector. This moreover simplifies cleaning and facilitates a multiple re-use of the valve head.

In one embodiment, the valve head is an integral component of the adapter. In this case, the whole adapter may be embodied as a valve head, i.e. the further sensors may be arranged distributed over the adapter and need not be situated adjacent to the connector to the breastmilk collection container.

In another embodiment, the valve head is detachably connectable to the adapter and/or the breastmilk collection container. This embodiment is particularly suitable as a retrofitting set.

Preferably, the fill level sensor and, if present, the at least one further sensor and, if likewise present, the electronics unit are protected against the ingress of liquid. Preferably, the valve head has a dishwasher-safe embodiment.

Further embodiments are specified in the dependent claims.

BRIEF DESCRIPTION OF THE DRAWINGS

A preferred embodiment of the invention is described below on the basis of the drawings, which merely serve for explanatory purposes and should not be construed as restrictive. In the drawings.

DESCRIPTION OF PREFERRED EMBODIMENTS

Figure 1:
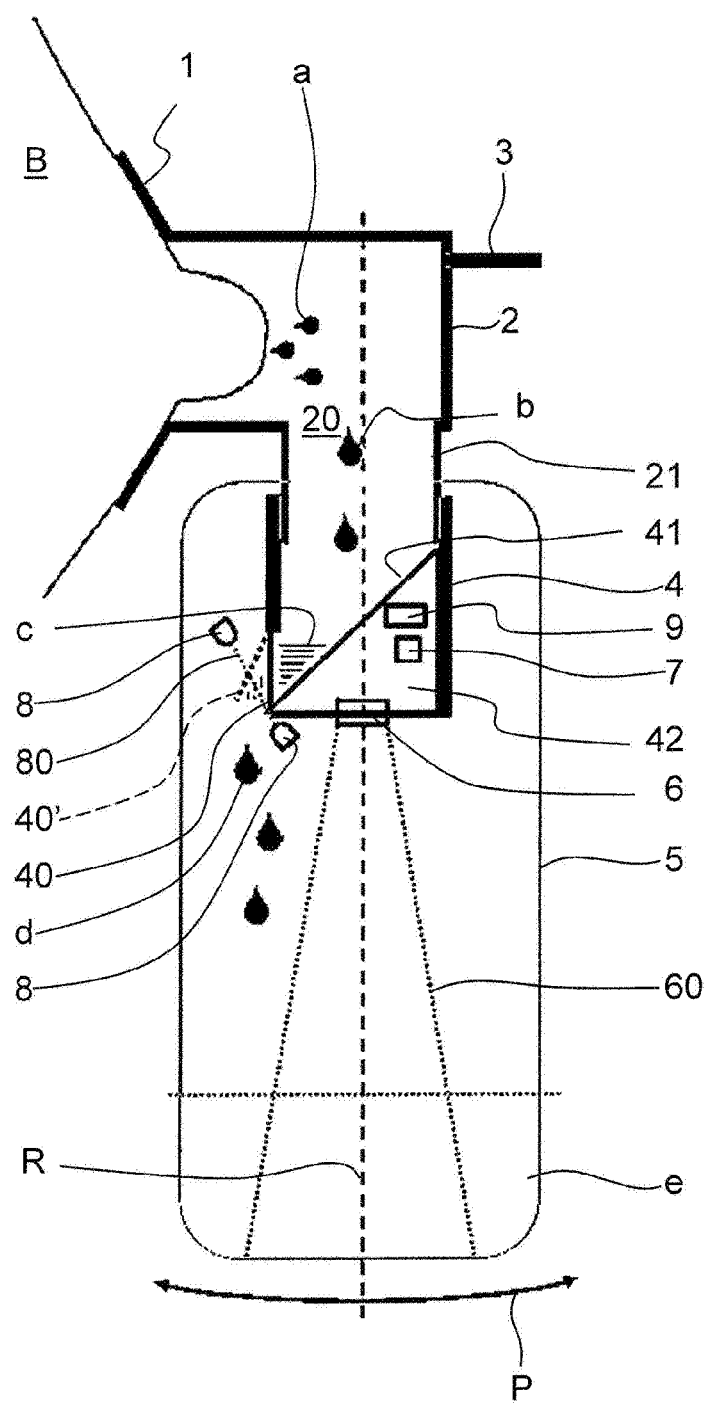
FIG. 1 shows a schematic illustration of a breast shield unit according to the invention when placed onto a mother's breast and FIG. 2 shows a schematic illustration of the breast shield unit in accordance with FIG. 1 in communication with external units.
Figure 2:
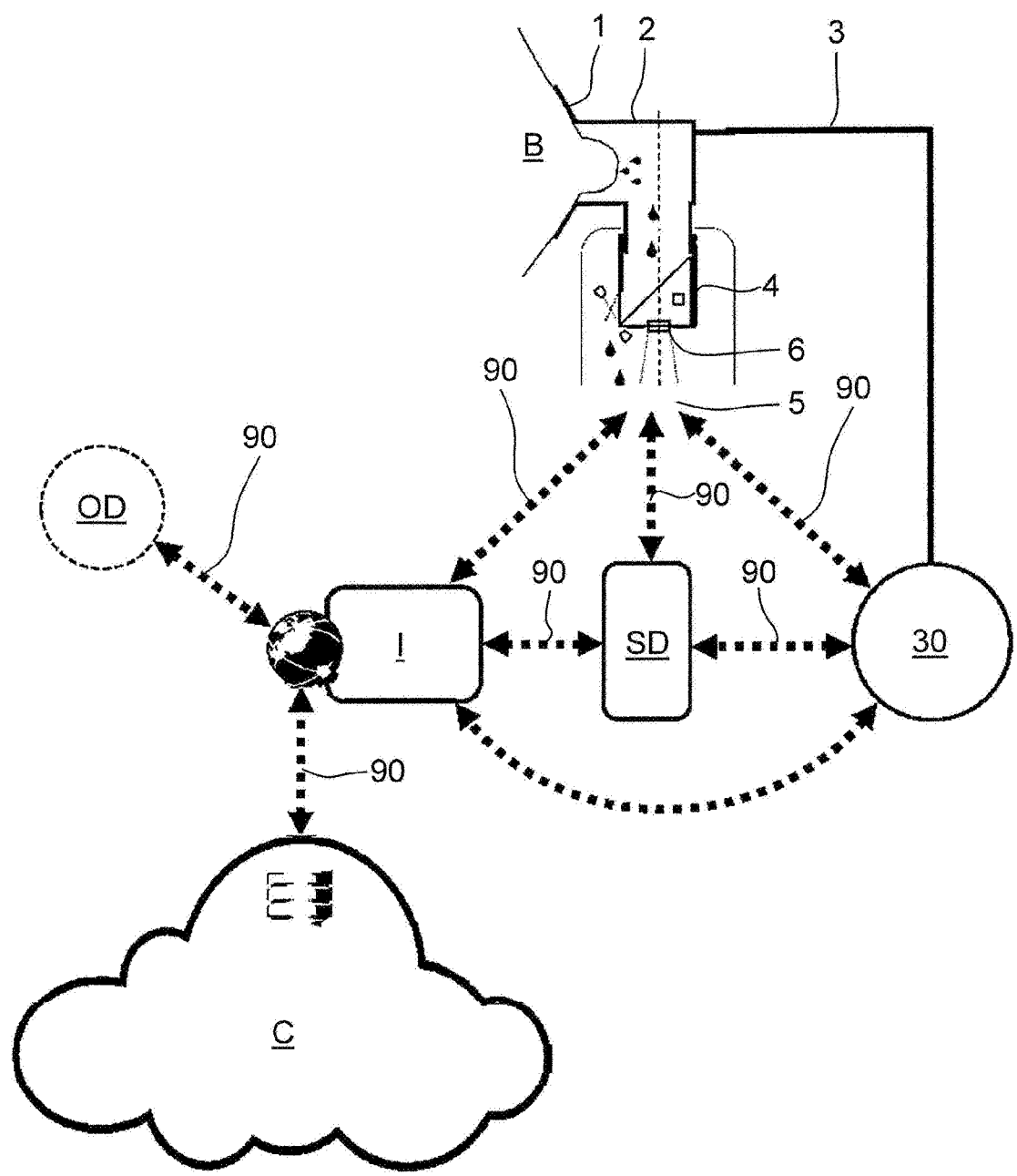

FIG. 1 depicts a breast shield unit according to the invention. It has a breast shield 1 for receiving a mother's breast B, in particular the nipple. The breast shield 1 is connected securely or preferably detachably to an adapter 2, which is also referred to as coupling part. The adapter 2 may be connected directly to a manually driven or electric-motor-driven breast pump. Preferably, as depicted here, said adapter is connected to the breast pump by way of a vacuum line 3, in particular by way of a silicone tube. The breast pump is depicted in FIG. 2 and provided there with the reference sign 30.

The adapter has an interior 20 which forms part of a breastmilk channel from the breast shield 1 to breastmilk collection container 5. The breastmilk collection container 5 is detachably fastened to a connection nozzle 21 of the adapter 2.

A valve head 4 is securely or detachably arranged at the adapter 2, said valve head 4 preferably being fixed in terms of position in relation to the adapter 2. By way of example, the valve head 4 has a common integral embodiment with the adapter 2 or it is connectable therewith by way of a plug-in or screw-in connection.

The adapter 2 and the valve head 4 are preferably manufactured from a rigid plastic. The breastmilk collection container 5 preferably has a rigid or semi-rigid embodiment. The breastmilk collection container 5 preferably also consists of plastic. It may have a transparent, semi-transparent or opaque embodiment.

The valve head 4 preferably protrudes into the breastmilk collection container 5. The valve head 4 has a check valve. In this exemplary embodiment, the valve has a valve flap 40 hinged thereon on one side. The reference sign 40' denotes the valve flap in the open position, the reference sign 40 in the closed position.

The path of the expressed breastmilk is indicated in FIG. 1 by individual breastmilk droplets. The breastmilk emerging from the mother's breast B is denoted by the reference sign a, the breastmilk flowing, usually falling, in the valve head 4 is denoted by b, the breastmilk collecting in front of the closed valve flap 40 is denoted by c and the breastmilk finally reaching the breastmilk collection container 5 is denoted by d. The pool of breastmilk in the breastmilk collection container 5, i.e. the breastmilk which has already been collected, is provided with reference sign e. Depending on the embodiment, the valve flap 40 opens on account of the prevalent pressure conditions during each suction cycle or only once enough breastmilk c has been collected in front of the flap in order to open the latter. Other ways of opening the valve are also possible.

A flow sensor 8, in this case an optical sensor embodied as a photoelectric barrier, is preferably present in the region of the valve flap 40. It appears to hover within the breastmilk collection container 5 in the schematic illustration in accordance with FIG. 1. However, it is likewise fastened to the valve head 4.

The flow sensor 8 measures the aperture angle of the valve flap 40. The capture region of the flow sensor 8, i.e. the light path, is provided with reference sign 80 in FIG. 1. The aperture angle of the valve flap 40 is approximately proportional to the amount of breastmilk d "flowing out". In order to optimize the measurement accuracy, the aperture angle of the valve flap 40 is preferably scanned with at least 30 measurements/second. As mentioned at the outset, this measurement signal is used to correct the measurement of the fill level sensor described below, particularly in the case of low fill heights. Moreover, this sensor renders it possible to determine whether and when the valve flap 40 has opened.

A fill level sensor 6 is arranged in an electronics region 42 of the valve head 4 which is separated from the breastmilk channel. The electronics region 42 is preferably embodied as a sealed chamber. By way of example, the separation from the remainder of the valve head may be effected by way of a separating wall 41. If the latter has an oblique embodiment, it moreover facilitates the breastmilk flow to the valve flap 40.

The fill level sensor 6 has a capture region 60 which is directed to the opposite base of the breastmilk collection container 5. Therefore, the fill level sensor 6 is preferably arranged at the lower end face of the valve head 4. Preferably, the fill level sensor 6 is situated on the longitudinal central axis of the breastmilk collection container 5 which, preferably, forms the axis of rotational symmetry R of the breastmilk collection container 5 at the same time. The fill level sensor 6 is preferably a distance sensor, preferably an optical distance sensor and more preferably a TOF sensor (time-of-flight sensor).

The TOF sensor measures a distance from the sensor surface to the breastmilk surface. A microcontroller of an electronics unit 9 converts this distance into a volume taking into account the bottle geometry. The emission, and hence the capture region 60 of the TOF sensor, is usually conical or collimated.

Moreover, a position sensor 7, in this case a movement sensor, is preferably arranged in the electronics region 42. This position sensor 7 measures the movement or tilt position of the valve head 4, and hence of the breastmilk collection container 5 connected thereto by way of the adapter 2. The signals or data are supplied to the aforementioned electronics unit 9, in particular to the same microcontroller. They serve to compensate the signals of the fill level sensor 6 in the case of tilt positions of the breastmilk collection container 5 and therefore increase the accuracy of the measurement. The tilt position is denoted by a double-headed arrow and the reference sign P in FIG. 1.

The fill level sensor 6 and the position sensor 7 are arranged with a fixed position in relation to one another; i.e., if one sensor is put into a tilt position and/or moved, the same applies to the other sensor as well. Preferably, the same also applies to the flow sensor 8. The breastmilk collection container 5 is likewise arranged with a fixed position in relation to the fill level sensor 6 and, where present, to the position sensor 7. This is carried out by way of the corresponding connection to the adapter 2 and the corresponding connection between adapter 2 and valve head 4.

The aforementioned electronics unit 9 is preferably likewise arranged in the electronics region 42 of the valve head 4. Preferably, it comprises an energy supply integrated in the valve head 4, in particular an energy store. Preferably, no cables or plug-in connections lead to the outside. The data transfer from the electronics unit 9 to the outside and, where present, from the outside to the electronics unit 9 as well preferably occurs in a wireless manner. The energy transfer is preferably likewise carried out in a wireless manner. The electronics region 42 is preferably sealed off from the outside in a fluid-tight manner.

FIG. 2 depicts various communication paths 90 from the breast shield unit according to the invention to external information storage and/or information-processing units. The measurement values provide the mother, lactation specialist or other expert with information about the amount of expressed breastmilk. Since the mother cannot necessarily see the breastmilk collection container 5 during the pumping action, this allows her to see the fill level amount on a display of the breast pump 30, on a smart device SD, such as e.g. her smart phone or her tablet, or on a different suitable machine. Furthermore, these data may be made available to the Internet by way of an Internet access unit I without further action by the mother. By way of example, they may be stored in a cloud C, suitable to this end, or transmitted to a different unit OD, for example a personal computer. These measured fill level amount curves may be used for simultaneous or subsequent optimization of pumping parameters or measurement algorithms. By way of example, pumping parameters include vacuum level and pumping frequency, duration of a stimulation program (let down) of the pump prior to an automatic or manual change to the expressive, i.e. normal, pumping process and the like.

The breast shield unit according to the invention and the valve head according to the invention facilitate a fill level measurement without a structural change of the breast shield and breastmilk collection container. Moreover, they facilitate a data interchange with external information storage and/or information-processing units.

What is claimed is:

1. A breast shield unit of a breast pump for expressing human breastmilk, the breast shield unit comprising a breast shield to be placed onto a mother's breast, a breastmilk collection container for receiving expressed breastmilk, an adapter for connecting the breast shield to the breastmilk collection container and a valve head, with a breastmilk channel extending from the breast shield into the breastmilk collection container through the adapter and the valve head, and the valve head comprising a valve, said valve closing and opening the breastmilk channel during a pumping action, wherein a fill level sensor for measuring a fill level of the breastmilk collection container is arranged in the valve head, wherein the fill level sensor is a distance sensor for measuring a distance from a surface of the expressed breastmilk situated in the breastmilk collection container.

2. The breast shield unit according to claim 1, wherein at least one further sensor is arranged in the valve head.

3. The breast shield unit according to claim 2, wherein one of the at least one further sensors is a flow sensor which measures the flow of expressed breastmilk through the valve.

4. The breast shield unit according to claim 3, wherein the flow sensor is an optical sensor which detects a deflection of a valve flap of the valve.

5. The breast shield unit according to claim 1, wherein one of the at least one further sensors is a position sensor which detects the position of the breastmilk collection container in three-dimensional space and hence an oblique position thereof in three-dimensional space.

6. The breast shield unit according to claim 5, wherein the position sensor is an acceleration sensor.

7. The breast shield unit according to claim 5, wherein the fill level sensor and the position sensor are arranged with fixed positions in relation to one another in the valve head.

8. The breast shield unit according to claim 1, wherein an electronics unit for processing signals from the fill level sensor is arranged in the valve head.

9. The breast shield unit according to claim 8, wherein at least one further sensor is arranged in the valve head and wherein the electronics unit is embodied to process signals of the at least one further sensor.

10. The breast shield unit according to claim 8, wherein the electronics unit is embodied to interchange data with at least one of the following units:
 a breast pump,
 a smart device, which is updated from an information technology point of view,
 an external data processing unit,
 a cloud,
 Internet, and
 an Internet access unit.

11. The breast shield unit according to claim 10 wherein the smart device is a smartphone.

12. The breast shield unit according to claim 10 wherein the external data processing unit is a computer.

13. The breast shield unit according to claim 1, wherein the valve head is embodied without wires to the outside and, without an electronic connector.

14. The breast shield unit according to claim 1, wherein the valve head is an integral component of the adapter.

15. The breast shield unit according to claim 1, wherein the valve head is detachably connectable to the adapter and/or the breastmilk collection container.

16. The breast shield unit according to claim 1 wherein the fill level sensor is a time-of-flight sensor.

17. The breast shield unit according to claim 1 wherein the valve head comprises an electronics region, which is separated from the breastmilk channel and wherein the fill level sensor is arranged in the electronics region.

18. A valve head of a breast shield unit of a breast pump for expressing human breastmilk, the breast shield unit comprising a breast shield to be placed onto a mother's breast, a breastmilk collection container for receiving expressed breastmilk, an adapter for connecting the breast shield to the breastmilk collection container and the valve head, with a breastmilk channel extending from the breast shield into the breastmilk collection container through the adapter and the valve head, wherein the valve head has a valve which closes and opens the breastmilk channel during a pumping action and wherein a fill level sensor for measuring a fill level of the breastmilk collection container is arranged in the valve head, wherein the fill level sensor is a distance sensor for measuring a distance from a surface of the expressed breastmilk situated in the breastmilk collection container.

19. The valve head according to claim 18 wherein the fill level sensor is a time-of-flight sensor.

* * * * *